(12) United States Patent
Durand et al.

(10) Patent No.: US 8,868,211 B2
(45) Date of Patent: Oct. 21, 2014

(54) NERVE CUFF FOR IMPLANTABLE ELECTRODE

(75) Inventors: Dominique M. Durand, Solon, OH (US); Dustin Tyler, Highland Heights, OH (US); Benjamin Cottrill, Cleveland, OH (US)

(73) Assignee: Case Western Reserve University, Cleveland, OH (US)

( * ) Notice: Subject to any disclaimer, the term of this patent is extended or adjusted under 35 U.S.C. 154(b) by 388 days.

(21) Appl. No.: 11/839,313

(22) Filed: Aug. 15, 2007

(65) Prior Publication Data

US 2008/0046055 A1    Feb. 21, 2008

Related U.S. Application Data

(60) Provisional application No. 60/822,403, filed on Aug. 15, 2006.

(51) Int. Cl.
*A61N 1/00* (2006.01)
*A61N 1/05* (2006.01)

(52) U.S. Cl.
CPC ............... *A61N 1/0556* (2013.01); *A61N 1/00* (2013.01)
USPC ........................................................ 607/118

(58) Field of Classification Search
CPC ................................. A61N 1/00; A61N 2/00
USPC ............... 24/1; 600/116, 118; 604/174, 175; 607/40, 116, 118
See application file for complete search history.

(56) References Cited

U.S. PATENT DOCUMENTS

| 4,112,951 | A | * | 9/1978 | Hulka et al. ............... 128/831 |
| 4,449,531 | A | * | 5/1984 | Cerwin et al. ............. 606/158 |
| 5,599,275 | A | * | 2/1997 | France ......................... 600/38 |
| 5,957,968 | A | * | 9/1999 | Belden et al. ............. 607/126 |
| 6,456,866 | B1 | | 9/2002 | Tyler et al. |
| 7,672,728 | B2 | * | 3/2010 | Libbus et al. .............. 607/42 |
| 2006/0116739 | A1 | * | 6/2006 | Betser et al. .............. 607/48 |
| 2006/0147492 | A1 | * | 7/2006 | Hunter et al. ............ 424/426 |

FOREIGN PATENT DOCUMENTS

DE        10028522 A1 * 12/2001

OTHER PUBLICATIONS

Schuettler et al., EPO Machine Translation of DE 10028522 A1, Dec. 20, 2001.*

Lertmanorat et al., "Electrode Array for Reversing the Recruitment Order of Peripheral Nerve Stimulation: Experimental Studies", Annals of Biomedical Engineering, vol. 34, No. 1, Jan. 2006, pp. 152-160.

* cited by examiner

*Primary Examiner* — Christopher D Koharski
*Assistant Examiner* — Elizabeth K So
(74) *Attorney, Agent, or Firm* — Tarolli, Sundheim, Covell & Tummino LLP

(57) ABSTRACT

A flat interface nerve electrode provides a plurality of electrical contacts embedded in a non-conductive cuff structure, which acts to gently and non-evasively redefine the geometry of a nerve through the application of a force acting on the nerve without causing damage to the nerve. The cuff is open at one side and has a connection to a lead at the other side. During implantation the open sides of the cuff are closed so as to capture the nerve in the cuff in a single motion.

20 Claims, 7 Drawing Sheets

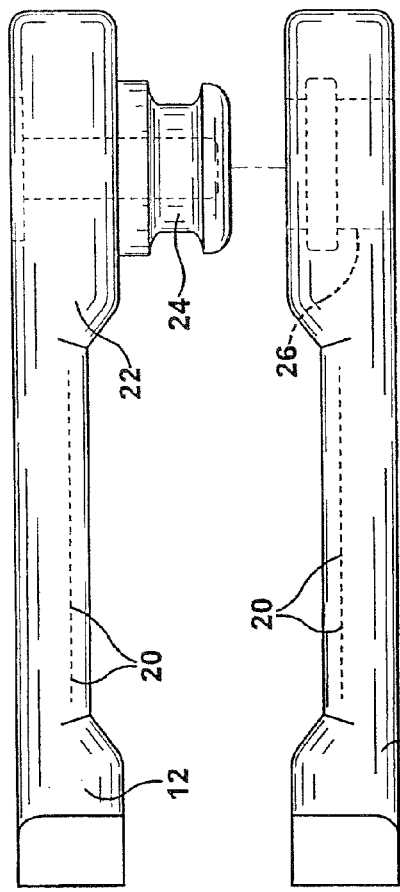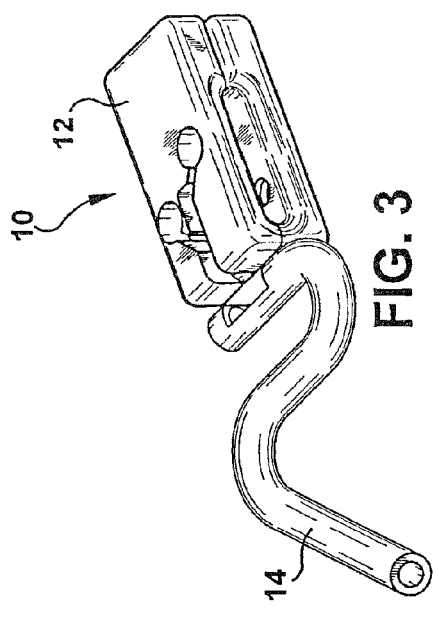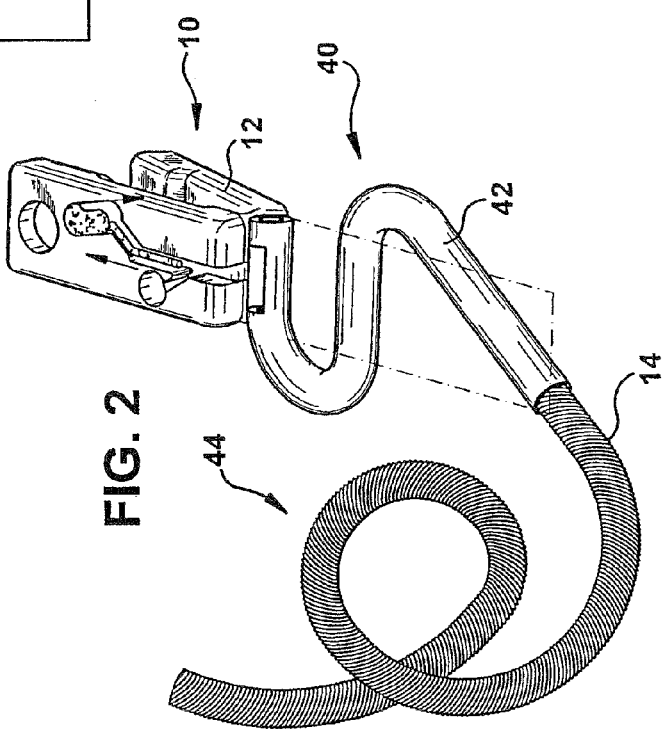

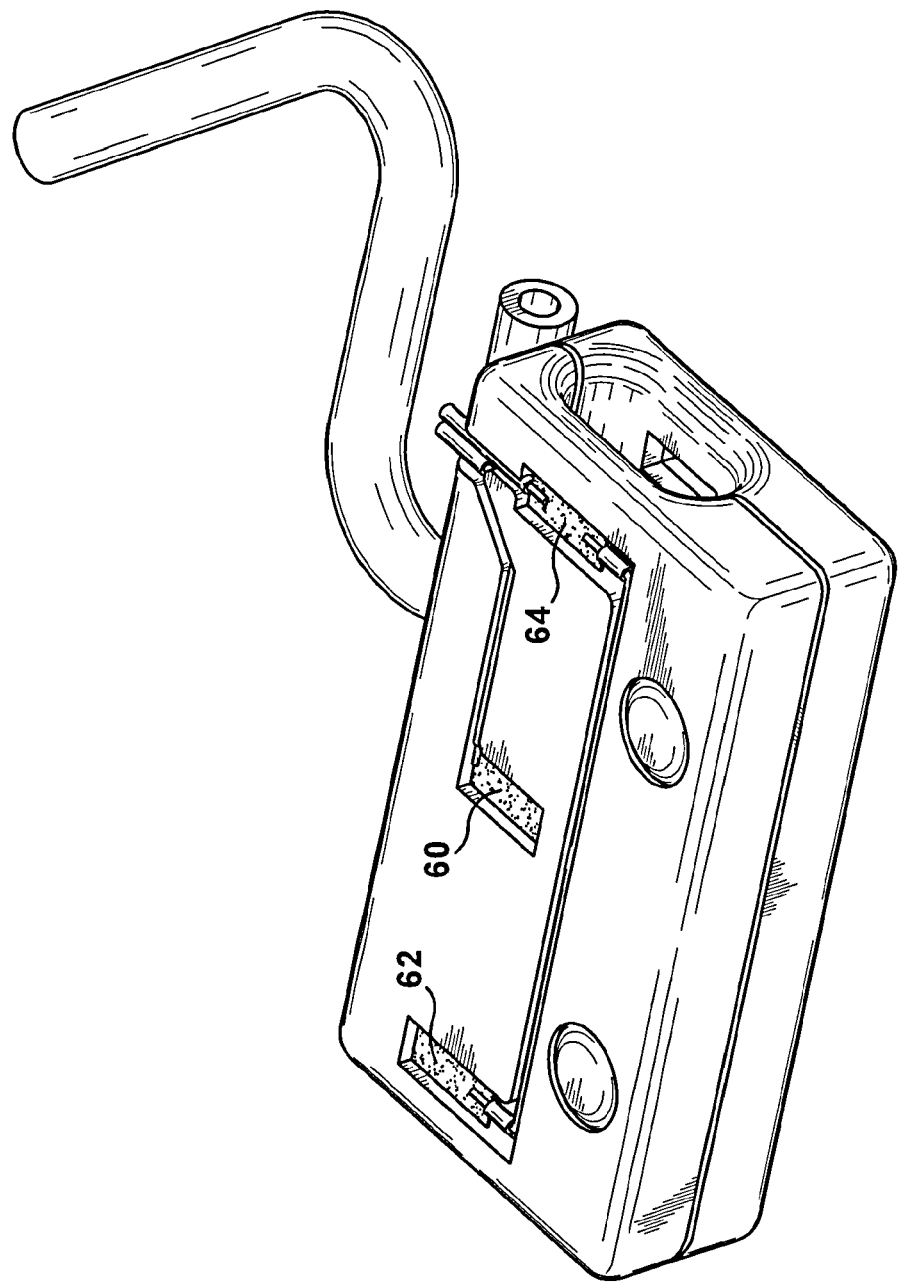

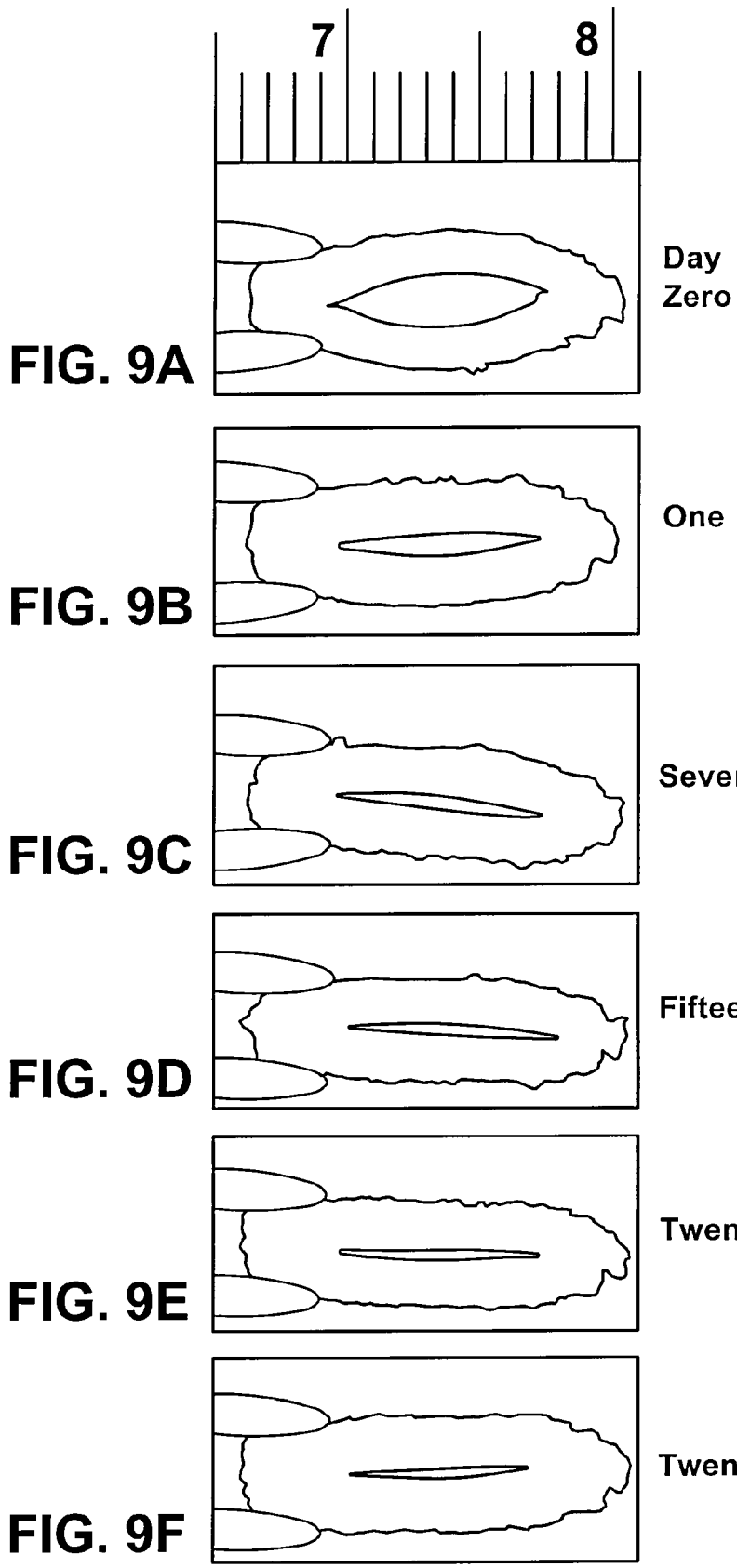

NERVE CUFF FOR IMPLANTABLE ELECTRODE

This application claims the benefit of U.S. Provisional Patent Application No. 60/822,403 filed 15 Aug. 2006, which is hereby incorporated in its entirety.

FIELD OF INVENTION

The invention relates to implantable biomedical devices and methods, and more particularly to a cuff for selectively stimulation and/or monitoring nerves or other biological soft tissue, and methods of using such a cuff, including use as an electrode

BACKGROUND

Medical therapies have been developed that depend on the implantation of devices to selectively stimulate or monitor a patient's nerves or other soft tissue. Functional electrical stimulation of the nervous system, for example, can be used to help to restore or maintain some degree of lost sensory and motor function in neurologically impaired individuals. In addition, there are certain specialized applications, such as the treatment of sleep apnea, where it is necessary to simultaneously monitor and generate electrical signals in nerves. Implantable electrical stimulation and/or recording devices include: (1) surface electrodes placed on the skin surface to activate nerves in a general region of interest; (2) intra muscular and epimysial electrodes to activate nerves to individual muscles; (3) the use of neural interfaces to address individual nerves; and (4) implantable cuff electrodes.

Cuff electrodes have been used for peripheral nerve stimulation and, among other advantages, generally require less energy to produce the desired effects than either surface or intra muscular electrodes. The smaller power requirement may result in a potentially safer long term therapy.

Half cuff electrodes generally have a C-shape cross-section, and cylindrical cuff electrodes can be spiral, helical, split-cylinder, or chambered cylinders. C-shape and split cylinder cuffs generally include a dielectric material defining a bore having sufficient diameter to receive a nerve trunk to be electrically stimulated. One or more contacts on the inner surface of the bore can be used to apply electrical stimuli or monitor nerve activity. The electrical stimuli, for example, may be used to provide functional electrical stimulation, to block neural nerve impulses traveling along the nerve trunk, or to cause other effects.

The spiral type of cuff electrode typically includes a self-curling sheet of non-conductive material biased-curl into a spiral. The spiral cuff also comes off the nerve very easily with a very small amount of force, and can rotate around the nerve, making it difficult to consistently identify and control the desired nerve fascicle. Conductive strips or pads disposed on the self-curling sheet along a line extending peripherally around the inner surface of the cuff. The conductive segments may be electrically conductive for applying electrical impulses or fluid conductive for infusing or extracting medications. In use, a first edge of a self-curling sheet may be disposed adjacent a nerve truck around which the cuff is positioned. The self-curling sheet is permitted to curl around the nerve forming an annular cuff.

The helix or helical cuff, similar to a telephone cord, acts as a spring due to its curved shape and allows a nerve to flex and permits more fluid exchange with surrounding tissue. This cuff must be wrapped around the nerve, which is time consuming and difficult. The helix cuff can be opened and placed over the nerve and there is no closure mechanism, the helix simply closes around the nerve when it is released. The helix cuff can be removed from the nerve, however, very easily and sometimes does not provide the desired proximity to the nerve fascicle of interest.

U.S. Pat. No. 6,456,866 discloses another type of nerve cuff that is particularly useful for functional electrical stimulation. The nerve cuff described in that patent made it easier to precisely position the nerve cuff on a nerve and then to stimulate or monitor selected fibers of the nerves. One application both monitors and generates electrical signals in the hypoglossal nerve for treatment of sleep apnea.

SUMMARY

The present invention provides an improved soft tissue cuff that is suitable for use as a nerve cuff electrode, for example. The improvements are related to one or more of: (i) closure of the electrode cuff, (ii) strain relief in the lead where it connects to the cuff, (iii) a slowly closing cuff, (iv) a recording electrode, and (v) an electrode with an array of contacts that enable reversing the recruitment order of axons in a nerve bundle.

More particularly, the invention provides a biocompatible cuff comprising a pair of members connected at a hinge end and securable together at a location removed from the hinge end via a closure mechanism that can secure the members in a closed condition.

The members can be made of silicon having a first hardness and the closure mechanism includes at least one element made from a material having a second hardness, which may be the same as or different from the first hardness. The closure mechanism can have a connector assembly with male and female elements that snap together. The closure mechanism can include multiple spaced-apart connector assemblies. The members and the closure mechanism can be molded as a single unit. The closure mechanism can include self-aligning features. The closure mechanism can be secured using a force applied along a common line of action.

The present invention also provides a method comprising the following steps: (a) placing a nerve cuff adjacent a nerve; and (b) closing the cuff around the nerve in a single step.

The invention also provides an electrode comprising a cuff and a lead extending from the cuff, where adjacent the cuff the lead passes through a resilient sleeve having a bent shape that reduces the transmission of forces from the lead to the cuff.

The bent shape can include a U-shape or an S-shape, for example, and the bent shape typically defines an angle of between 45 and 180 degrees.

The present invention also provides a system for functional electrical stimulation comprising a cuff for a nerve or muscle filament. The cuff includes an elastic collar that exerts a force on the filament to cause the filament to gradually reshape to the internal configuration of an opening in the collar. The resulting pressure in the filament is less than 80 mmHG, and the elastic collar includes a biodegradeable material that dissolves in a body and thereby changes the pressure profile and reshapes the filament to the internal configuration of the opening in the collar.

The present invention also provides a method for functional electrical stimulation comprising the following steps: (a) providing a stimulation apparatus, which, when operated, stimulates a nerve or muscle filament; (b) providing a monitoring apparatus, which, when operated, monitors a biological property of a nerve or muscle filament; (c) placing a cuff around a nerve or muscle filament; and (d) applying a gradual force to the nerve or muscle filament by means of the cuff which results in a pressure in the nerve or muscle filament of less than 80 mmHg; operating the stimulation apparatus and; operating the monitoring apparatus.

The foregoing and other features of the invention are shown in the drawings and particularly pointed out in the claims. The following description and annexed drawings set forth in detail one or more illustrative embodiments of the invention; this being indicative, however, of but one or a few of the various ways in which the principles of the invention might be employed.

BRIEF DESCRIPTION OF DRAWINGS

FIG. 2 is a perspective view of a flat interface nerve electrode (FINE) provided by the present invention in an open condition.

FIG. 3 is a perspective view of the FINE of FIG. 2 in a closed condition.

FIG. 4 is an enlarged partial side view of a portion of the FINE of FIG. 3.

FIG. 5 is a perspective view of another embodiment of the FINE in a closed condition.

FIGS. 9A-F are a sequence of images showing the process of the slowly closing embodiment closing over a period of time.

DETAILED DESCRIPTION

Figure 1A:
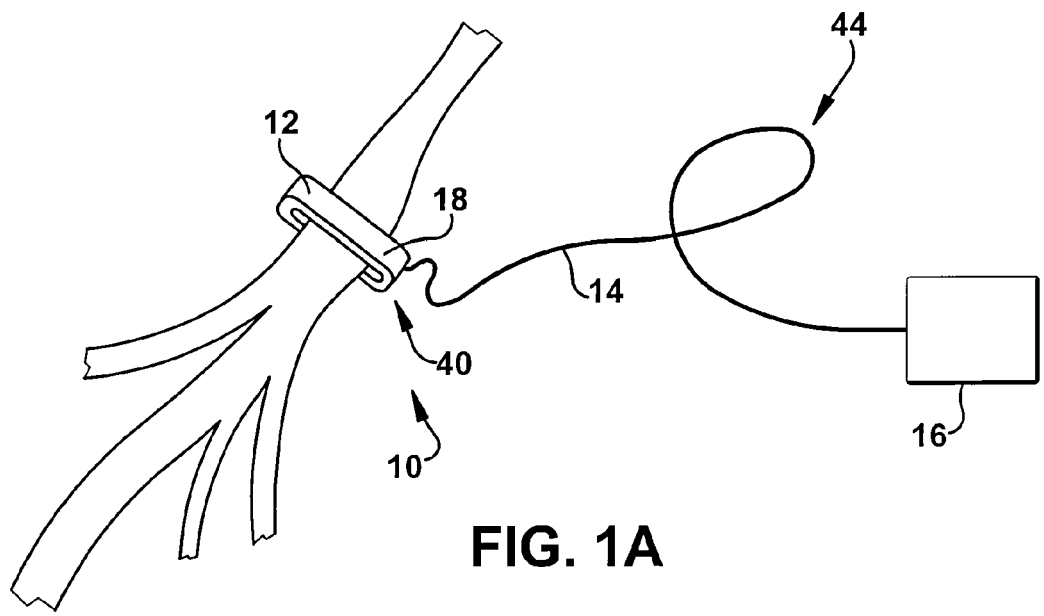
FIG. 1A is a schematic view of an exemplary system for functional electrical stimulation with a cuff applied to a nerve and a lead extending from the cuff to a control unit.
Figure 1B:
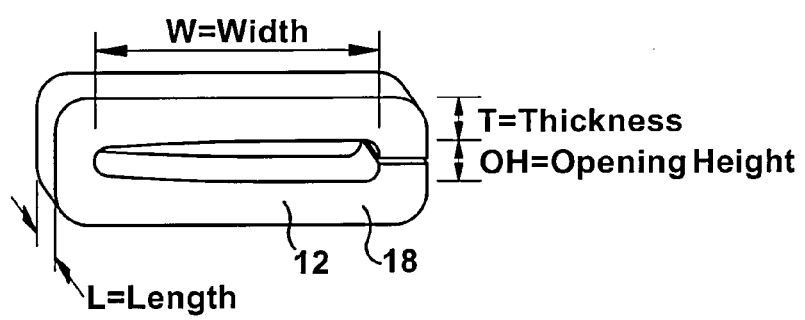
FIG. 1B is a schematic perspective view of a cuff.

The present invention provides one or more improvements to a cuff that can be used as part of an electrode, and particularly improves on the flat interface nerve electrode (FINE) disclosed in U.S. Pat. No. 6,456,866, which is hereby incorporated by reference. Although the cuff is described primarily as providing electrical contacts for electrically stimulating or monitoring a nerve, the cuff may be adapted for use with other soft tissue, such as muscle. In addition or as an alternative to the electrical capabilities of the cuff, the cuff can be adapted to act as a chemical dispenser or sensor. To simplify the description, the term "electrode" includes cuff designs for chemical dispensing or sensing that lack electrical signal capabilities.

Referring now to the drawings, and particularly to FIGS. 1-4, the electrode 10 includes a cuff 12 and a lead 14 extending from the cuff 12 to a control unit 16. The cuff 12 includes a non-conductive band 18 with electrical contacts 20 molded into the band. In use, the band 18 encircles a nerve and gently and non-invasively applies a defined exterior force over time to redefine the geometry of the nerve, such as by flattening, thereby laterally spreading the fibers or fascicles within the nerve for selective stimulation or monitoring or both.

The driving force that urges the band inward is provided by mechanical spring action at the active end of the cuff as well as the elastic nature of the cuff material. The illustrated design allows superficial placement of the electrical contacts with selective access to the entire axon population, with minimal damage to the nerve itself. The contacts are each capable of monitoring or activating separate and distinct regions within the nerve, along both the longitudinal and radial axis of the nerve, which generally was not previously accessible by other types of electrode cuffs. The electrode also is capable of sensing small neural signals with better signal to noise ratios due to the close proximity of each of the contacts to separate axons comprising the fascicles.

The lower limit of applied pressure required to reshape the nerve is something greater than that which is naturally occurring in an occurring nerve. This pressure is usually in the vicinity of 2 mmHG.

It is to be appreciated that by controlling the spring constant or force exerted by the cuff surfaces, the cuff can be configured to rest against the surfaces of the epineurium membrane. The desired pressure, which results from the force applied by the cuff, is from about 2 to about 80 mmHG; more preferably from about 3 to about 30 mmHG, and most preferably from about 5 to about 15 mmHG.

The flat interface nerve electrode (FINE) shown applies small forces on opposing sides of the nerve while allowing room for the nerve to expand to the sides. In general, a small force does not significantly decrease nerve blood flow and will reshape the nerve into an elongated or flattened oval geometry that approximates the "ideal" geometry of a flat cable.

Each of the plurality of electrical contacts 20 are individually connected to the lead 14 to the control unit 16, which can include an electrical signal generating source or monitoring device. Fine conductive wires embedded in the band 18 extend from the contacts to a location at an edge of the band to which the lead is attached. In this way, the conductive wires are insulated from direct contact with either the nerve, other conductors, or other surrounding tissue. Also, the non-conductive band acts as a reinforcing structure and affords a level of structural integrity to the somewhat otherwise frail conductors.

Although the illustrated embodiment shows the electrical contacts molded into the band, one alternative includes forming a micro-multi-contact array in silicon using semiconductor fabrication technology. In this way, active and intelligent electronics may be included on the cuff itself.

In use, the subject nerve is surgically accessed and the open side of the cuff is slipped over the nerve in the desired position. The cuff is opened as is shown in FIG. 2 and placed around the nerve. At this point, the distal ends of the band are brought together in a single step to secure the cuff in place, completely encircling the nerve.

The FINE is shown as a pair of beams closed at the ends to form a continuous band with a rectangular opening. The opening is not limited to a rectangular shape, however. When the cuff is first placed around a nerve, the beams are deformed around the nerve. The thickness (t), width (w), length (l), and cross-sectional profile of the beams, as well as the properties of the selected material, will determine the magnitude of the force that will be applied to the nerve.

The following paragraphs describe improvements to the electrode, primarily to the structure of the cuff and the lead connected to the cuff. These improvements are related to (i) closure of the cuff, (ii) strain relief in the lead where it connects to the cuff, (iii) a slowly closing cuff, (iv) a recording electrode and (v) an electrode with an array of contacts that enable reversing the recruitment order of axons in a nerve bundle.

(i) Closure

The current FINE has a cuff with a pair of beam- or plate-like members 22 connected together at a hinge side to form a pivoting clamp-like structure. In previous embodiments of the FINE, the cuff was closed with a suture after the beam-like members had been placed around a nerve. The resulting band surrounded the nerve and held the cuff in place relative to the nerve. Given the size of the cuff, which can have a major dimension that is less than 20 mm, closing such a cuff with a suture can be difficult to do during surgery.

The improvement provides a one step closure mechanism whereby the two opposing beams are brought together and corresponding surfaces of the beams are held together at a particular spacing in a single step. In other words, the cuff is closed in a single motion, pushing the opposing beams together, twisting the beams or otherwise moving the beams from an open state to a closed state in a single motion without a change in direction.

Figure 6:
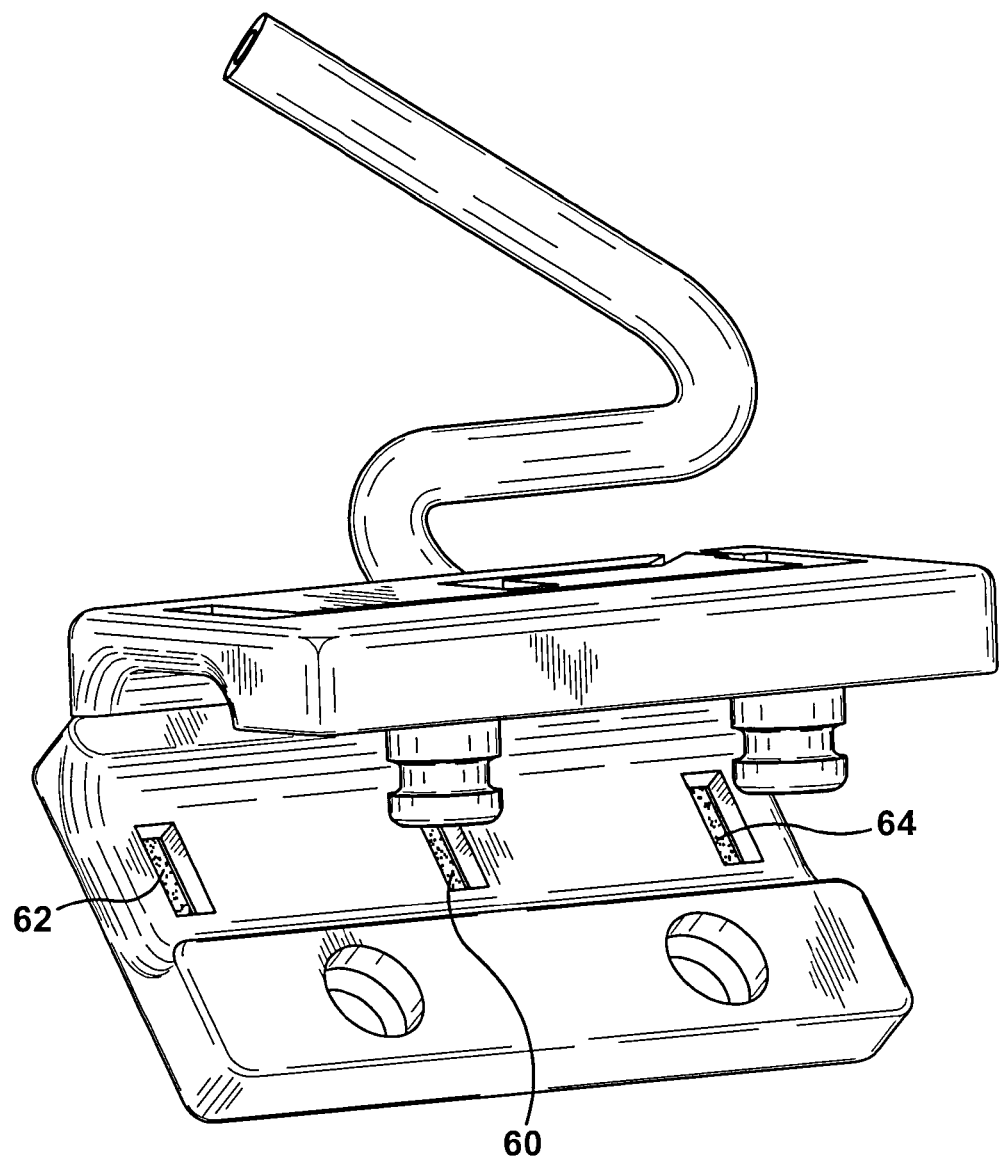
FIG. 6 is a perspective view of the embodiment of FIG. 5 in an open condition.

An exemplary cuff is made primarily of silicone, and in particular silicone with a range of hardness of about 30 to 90 Shore A, and more particularly about 40 to 70 Shore A. The closure mechanism can be formed of a silicone having a hardness that is different than the silicone used in the cuff, but in an exemplary embodiment a substantial portion of the cuff is molded as a single unit. The closure mechanism is molded at the same time as the cuff and includes male 24 and female 26 mating parts that come together with a snap closure. The exemplary closure mechanism is self-aligning. Alternatively, the male parts can be added or otherwise formed in a subsequent step. The force required to disengage the mating parts must be sufficient so that the closure mechanism will remain closed. If sufficient force is applied, however, the closure mechanism must open before it damages the nerve. An estimated force for closing the closure mechanism is less than about 2 N (about 0.5 lbf.). The embodiment shown in FIGS. 2-4 has a closure mechanism with a single male-female-snap-connection connecting assembly. Longer or wider cuffs can have multiple connecting assemblies, as shown in FIG. 6, for example.

The closure mechanism is not limited to the illustrated male and female snap closure elements. In addition to or as an alternative to the described snap closure, the cuff may include an adhesive or cohesive, a sliding or pivoting dovetail-type connection, or micro-hook-and-loop fasteners, for example.

Other types of cuff electrodes have required more effort to close. One type of cylinder cuff has a piano hinge closure mechanism on one side where a pin (in the form of a flexible suture) is used to close the piano hinge. This is a multi-step process, however. First the cylinder is closed, then a suture is threaded through the hinge parts and then finally tied off and trimmed. The cylinder-type cuff also would benefit from the closure mechanism described herein for the FINE cuff.

(ii) Strain Relief

In any electrical connection where a cable, such as for power or data, is connected to a device there is a mechanical weak point at the connection point where failure is likely to occur.

In the case of an implantable electrode, it would be desirable to minimize the force applied to the cuff 12, and thus to the nerve, by the lead 14, as well as to minimize stress on the material where the lead attaches to the cuff. In this case, a bent shape 40, such as an S-shape or a U-shape, is formed in the lead adjacent the cuff and a resilient sleeve 42 is molded in that shape so that the lead will retain its shape in the absence of any strain forces. When an axial (pulling) force is applied to the lead, e.g., the bent shape straightens out until the bend disappears before significant force is transferred to the cuff. This provides strain relief particularly in the longitudinal (along the general axis of the lead), translational (side-to-side transverse to the longitudinal direction) and even some torsional strain relief (twisting or rotating forces).

The surgeon implanting the electrode typically forms a loop, as shown at 44, in the lead 14 during the surgical procedure, and this loop provides gross strain relief for larger forces applied to the lead. The bent sleeve 42 adjacent the cuff provides local relief on a smaller scale and reinforces the connection between the lead and the cuff. It also allows the lead to extend from the cuff, and thus from the nerve, at any angle while retaining substantially uniform flexibility in all directions transverse the longitudinal direction.

This concept of providing strain relief is generally applicable to any type of cuff, and is not limited to the FINE cuff.

(iii) Slowly Closing

Figure 7:
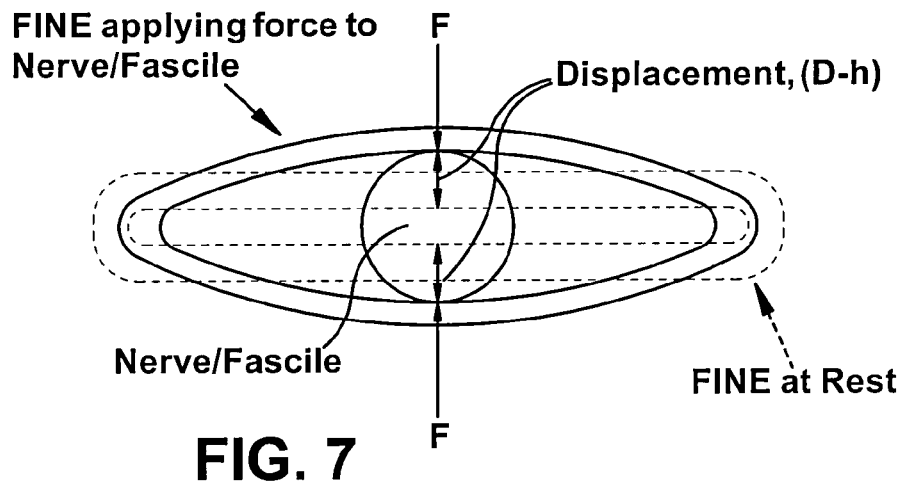
FIG. 7 is a schematic view of a cuff as initially placed around a nerve illustrating the forces applied to the nerve.

The slowly closing cuff is intended to reduce the stress on a nerve that is being flattened by having a cuff placed thereon. As shown in FIG. 7, at rest the cuff has a generally rectangular shape that is stretched out of shape when initially secured around the nerve. The cuff material applies a force F to the nerve as it returns to its original shape and deforms the nerve.

The slowly closing cuff generally is designed with an opening height larger than the size of the nerve to accommodate initial swelling. The cuff closes slowly to reshape the nerve into the desired flat geometry. The cuff is created by combining the reshaping properties of the FINE and the controllable degradation of Poly (DL lactic-co-glycolic) acid (PLGA). Bonding 50/50 or 65/35 PLGA to a stretched FINE can increase the opening heights (OH) on average from 0.1 mm to 1.66±0.45 and 2.05±0.55 mm respectively. The addition of the PLGA films controls the time course of closure over a period of 16±1 days and 14 to 16 hours for the 50/50 and 65/35 slowly closing cuffs respectively.

Figure 8A:
FIGS. 8A-8D are a sequence of schematic views of a slowly closing embodiment of the cuff provided by the present invention.
Figure 8B:
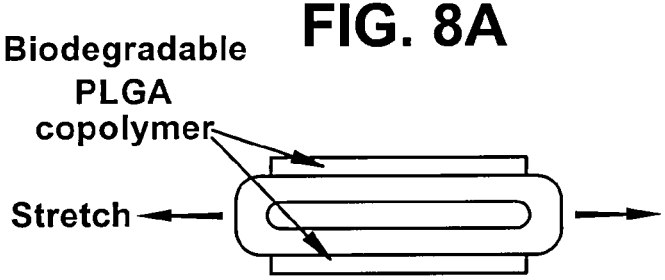
Figure 8C:
Figure 8D:

In the slowly closing embodiment shown in FIGS. 8A-8D, a biodegradable material can be used to slowly change the forces exerted by the cuff over time as the material degrades in the patient's body. The regular cuff material provides a base. The base material is stretched and a biodegradable polymer is bonded onto the stretched base (FIG. 8B). This bi-layer cuff is then closed around the nerve in the usual fashion, and the polymer degrades over time. As it degrades, the base material will want to return to its original, typically flat, shape. Thus, the nerve is flattened slowly over time.

The flat interface nerve cuff slowly applies transverse pressure to opposing surfaces of the nerve, so as to spread the fascicles and flatten the epineurium membrane of the target nerve. This flattening action effectively allows the electrical contacts to interact with particular fascicles through the epineurium membrane without puncturing either the perineurium membrane, or the epineurium. Typically, the time period required for the cuff to function properly extends from about one (1) hour to several days depending upon particular application and situation.

This process is further illustrated in FIGS. 9A-9F. These time-lapse images show the change in the shape of the opening defined by the cuff over a period of time, in this case twenty-eight days. As shown in FIG. 9A, the opening in the cuff is substantially oval at the start. Over time, as shown in FIGS. 9B-9F, the biodegradable polymer degrades until the opening in the cuff returns to a rectangular slit.

(iv) Recording

For recording—monitoring nerve signals, for example—a pair of reference ground points are provided on opposite sides of a recording electrical contact along the length of the channel for receiving a nerve. The embodiment shown in FIGS. 5 and 6 includes one recording contact 60 with a pair of reference grounds 62 and 64 equally spaced on opposing sides of the recording contact. The equidistant spacing helps to reduce noise and stimulation artifacts, thereby improving the electrode's sensitivity to a compound action potential in a target nerve. More than one recording contact can be placed between the ground points. This recording arrangement also can be used for stimulating the target nerve, but this design does not provide as much selectivity as the non-recording embodiment. The recording electrode thus can provide simultaneous recording and selective stimulation of the desired nerve fascicles.

(v) Reversing Recruitment Order

Figure 10A:
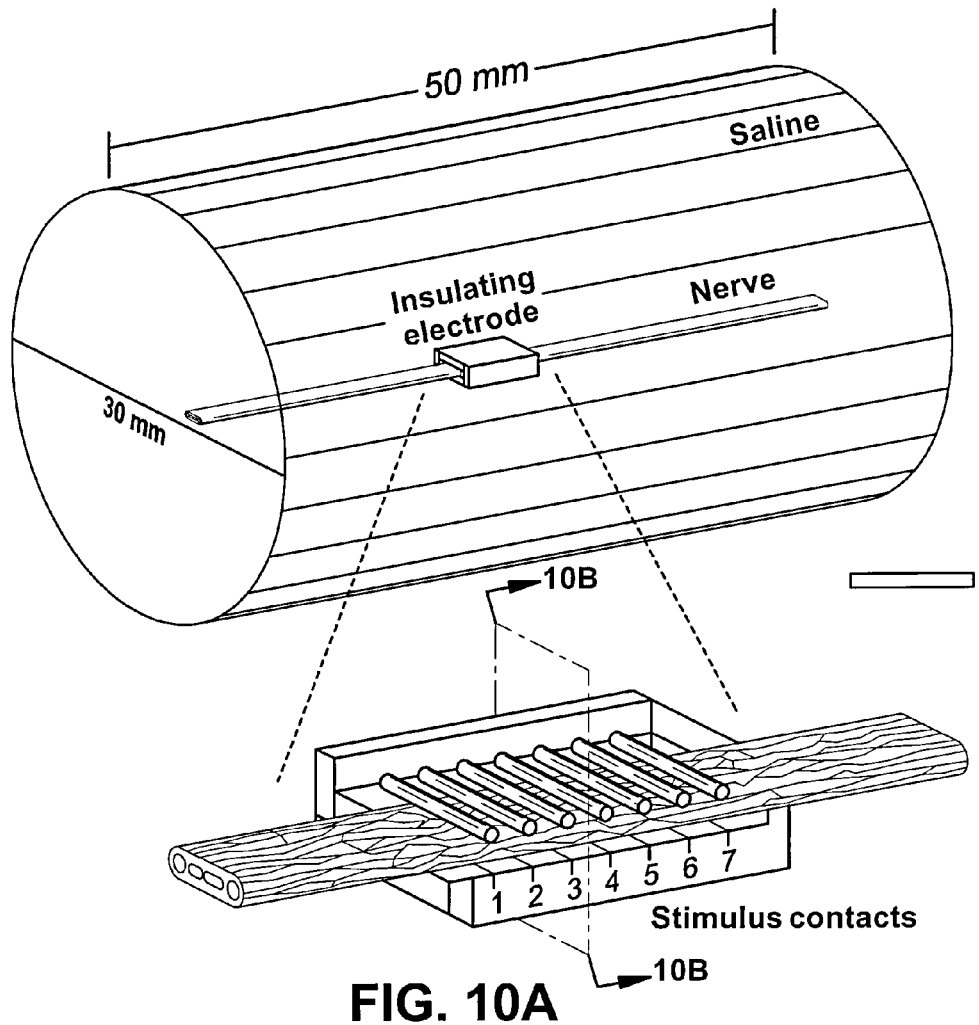
FIG. 10A is a perspective view of a model of a cat lateral gastrocnemius (LG) nerve and an electrode provided by the present invention.
Figure 10B:
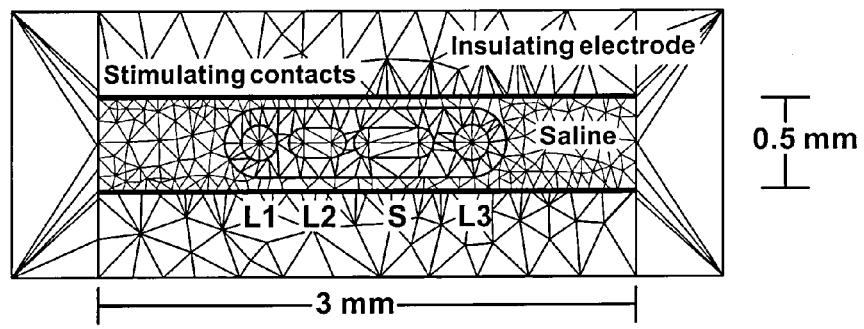
FIG. 10B is a cross-sectional view of the electrode and LG nerve of FIG. 10A.

In this improvement to the FINE, an example of which is shown in FIGS. 10A and 10B, a plurality of contacts are arrayed along the direction of a cat lateral gastrocnemius (LG) nerve in multiple rows, with each contact aligned with the axons in the nerve and the spacing dependent on characteristics of the axons in the nerve. These contacts make it possible to recruit smaller fascicles first before recruiting the larger fascicles. This is the opposite of the normal situation for the previous FINE. In other words, this allows for selectively recruiting axons or fascicles by diameter as well as selecting the desired fascicles that produce a desired effect. This concept requires additional multiplexing of the data signals, but may allow the electrode cuff to be used with more complex nerves, such as the sciatic nerve, for example. Trial and error can be used to determine which contacts produce a desired effect, such as control of the foot and ankle. Once the contacts that produce the desired effect are identified, those contacts can be permanently assigned to monitoring or stimulating their respective fascicles to achieve the desired results.

Although the invention has been shown and described with respect to certain preferred embodiments, equivalent alterations and modifications will occur to others skilled in the art upon reading and understanding this specification and the annexed drawings. In particular regard to the various functions performed by the above described integers (components, assemblies, devices, compositions, etc.), the terms (including a reference to a "means") used to describe such integers are intended to correspond, unless otherwise indicated, to any integer which performs the specified function of the described integer (i.e., that is functionally equivalent), even though not structurally equivalent to the disclosed structure which performs the function in the herein illustrated exemplary embodiment or embodiments of the invention. In addition, while a particular feature of the invention might have been described above with respect to only one of several illustrated embodiments, such feature can be combined with one or more other features of the other embodiments, as can be desired and advantageous for any given or particular application.

We claim:

1. A biocompatible cuff, comprising:
a pair of members pivotably connected at a hinge end to transfer from an open state to a closed state in a single motion and securable together at a location removed from the hinge end via a closure mechanism that can secure the members in a closed state;
the pair of members bonded with a biodegradable material that dissolves in a body,
where the biodegradable material is configured to cause a pressure profile of the cuff to change as the biodegradable material degrades.

2. A cuff as set forth in claim 1, where the closure mechanism has a connector assembly with male and female elements that snap together.

3. A cuff as set forth in claim 1, where the closure mechanism includes multiple spaced-apart connector assemblies.

4. A cuff as set forth in claim 1, where the members and the closure mechanism are molded as a single unit.

5. A cuff as set forth in claim 1, where the closure mechanism includes self-aligning features.

6. A cuff as set forth in claim 1, where the closure mechanism can be secured using a force applied along a common line of action.

7. A biocompatible cuff, comprising:
a pair of members pivotably connected at a hinge end to transfer from an open state to a closed state;
the pair of members being securable together at a location removed from the hinge end via a closure mechanism;
the pair of members having an internal opening height larger than the size of a nerve or muscle filament to which the biocompatible cuff is configured to be attached;
the pair of members bonded with a biodegradable material that dissolves in a body housing the nerve or muscle filament, where the biodegradable material is configured to cause a pressure profile of the cuff to change as the biodegradable material degrades; and
a closure mechanism configured to secure the members in a closed state;
the closure mechanism comprising self-aligning features.

8. The biocompatible cuff of claim 7, where the biocompatible cuff is configured to flatten over time to allow one or more electrical contacts in the cuff to interact with particular fascicles of the nerve, and where the pressure applied by the cuff increases as the biocompatible cuff flattens.

9. A biocompatible cuff, comprising:
a pair of members configured to enclose a fiber, where the pair of members are pivotably connected at a hinge end to transfer from an open state to a closed state in a single motion;
a closure mechanism configured to secure the members together at a location removed from the hinge end;
a biodegradable material that is bonded to at least one member of the pair of members and that holds the at least one member in a first position that creates an internal opening between the pair of members when the closure mechanism is secured; and
where the biodegradable material is configured to change the forces exerted by the cuff over time as the biodegradable material degrades.

10. The biocompatible cuff of claim 9, further comprising:
a set of electrodes for applying functional electrical stimulation to a fiber enclosed by the pair of members, where each electrode in the set of electrodes is configured to activate within the fiber, and where the set of electrodes is integrated on an inside surface of at least one of the pair of members.

11. The biocompatible cuff of claim 10, where the cuff is configured to flatten over time to allow one or more members of the set of electrodes to interact with particular fascicles of the nerve.

12. The biocompatible cuff of claim 9, where the pair of members is configured to apply transverse pressure to opposing surfaces of a nerve to spread fascicles in the nerve and to flatten an epineurium membrane of the nerve.

13. The biocompatible cuff of claim 9, where the biocompatible cuff is a flat interface nerve cuff having a substantially oval shape before the biodegradable material dissolves and having a substantially rectangular slit opening after the biodegradable material dissolves.

14. The biocompatible cuff of claim 9, where the cuff is configured to flatten over time to return to an original flat shape.

15. The biocompatible cuff of claim 14, where the cuff is configured with PLGA (DL lactic-co-glycolic acid) configured to degrade and to cause the cuff to flatten over a period of 16 days plus or minus 1 day.

16. The biocompatible cuff of claim 9, where the biodegradable material is composed of a combination of materials to cause the biodegradable material to degrade over a period of 28 days.

17. The biocompatible cuff of claim 9, where the cuff is configured with PLGA (DL lactic-co-glycolic acid) configured to degrade and to cause the cuff to flatten over a period of 14 to 16 hours.

18. The biocompatible cuff of claim 9, where the shape of the cuff changes over time as the biodegradable material degrades.

19. The biocompatible cuff of claim 9, where the closure mechanism is self-aligning.

20. The biocompatible cuff of claim 19,
where the closure mechanism being configured to close upon application of a force of less than 2 Newtons (N),
where the closure mechanism includes multiple spaced-apart connector assemblies, and
where the closure mechanism is configured to be secured by applying a force along a common line of action.

* * * * *